United States Patent [19]

Ritchey et al.

[11] Patent Number: 4,686,102

[45] Date of Patent: Aug. 11, 1987

[54] MULTIVALENT PNEUMOCOCCAL VACCINE AND PREPARATION THEREOF

[75] Inventors: Mary B. Ritchey, Norwood; Francis R. Cano, Mahwah, both of N.J.; Gerald J. O'Hara, Pearl River, N.Y.; James D. English, Oradell, N.J.; Wenlii Lin, New City, N.Y.

[73] Assignee: American Cyanamid Company, Stamford, Conn.

[21] Appl. No.: 599,318

[22] Filed: Apr. 12, 1984

[51] Int. Cl.$^4$ .......................................... A61K 39/116
[52] U.S. Cl. ...................................... 424/92; 424/88; 514/54; 536/1.1; 536/123; 536/127
[58] Field of Search ............... 424/92, 88; 260/712 R; 536/1.1, 123, 127; 514/54

[56] References Cited

U.S. PATENT DOCUMENTS 4,242,501 12/1980 Cano et al. ............................ 424/92

FOREIGN PATENT DOCUMENTS 0002404 6/1979 European Pat. Off. .............. 424/92

OTHER PUBLICATIONS

Bargono et al., "Vaccination and Revaccination with Polyvalent . . . Infant", *Proc. for Soc. of Exp. Biol. and Med.* 157, 1978, pp. 148–154.
Smit et al., Abst. #39335.
Hellerman et al., Abst. #28387.
Cowan et al., Abst. #20714x.
Robbins et al., Consideration for Formulating the Second-Generation Pneumococcal Capsular Polysaccaride Vaccine . . . Groups, *J. Infect. Dis.*, 148(6), 1983, p. 1136.
Douglas et al., Antibody Response to Pneumococcal Vaccination . . . Age, *J. Inf. Disease*, 148(1), 1983, p. 131.
C.A. vol. 90, #20714x, Pneumococcal Polysaccharide Immunization . . . Children, Cowan et al.
Abst. Howie et al., Use of Pneumococcal Polysaccharide Vaccine . . . Gp . . . *Pediatrics*, 73(c), 1984, pp. 79–81.
Abst. Hansman, Sereotypes in Pneumococcal Disease . . . 1978, *Aust. N. Z. J. Med.* 13(4), 1983, p. 359.
Abst. Gerichter et al., Survey of Pneumococcal Types in Israel, *Irs. J. Med. Sci.*, 19(6), 1983, pp. 520–523.
Abst. De Bac et al., A Multicentric Study for Serotypes . . . Holy, *Ric. Clin. Lab.*, 11(2), 1981, pp. 145–150.

*Primary Examiner*—John Kight
*Assistant Examiner*—Garnette D. Draper
*Attorney, Agent, or Firm*—Edward A. Conroy, Jr.

[57] ABSTRACT

A multivalent pneumococcal vaccine consisting of immunogenic amounts of purified pneumococcal capsular polysaccharide (substantially absent "C" polysaccharide) of pneumococcal types (Danish designation) 1, 2, 3, 4, 5, 6B, 7F, 8, 9N, 9V, 10A, 11A, 12F, 14, 15B, 17F, 18C, 19A, 19F, 20, 22F, 23F and 33F, and from none to one or both of 6A and 25, and combinations thereof and methods of purifying pneumococcal capsular polysaccharide types 3, 5, 9V, 10A, 11A, 15B, 17F, 19A, 22F and 33F.

10 Claims, No Drawings

MULTIVALENT PNEUMOCOCCAL VACCINE AND PREPARATION THEREOF

BACKGROUND OF THE INVENTION

This invention is concerned with a multivalent pneumococcal vaccine consisting of purified pneumococcal capsular polysaccharide with the "C" polysaccharide substantially absent. This invention is also concerned with the specific purification of each of 10 pneumococcal types which by Danish designation are types 3, 5, 9V, 10A, 11A, 15B, 17F, 19A, 22F and 33F to yield the purified immunogenic polysaccharides of the invention. Other pneumococcal types, found in the multivalent pneumococcal vaccine of this invention, which by Danish designation are types 1, 2, 4, 6A, 6B, 7F, 8, 9N, 12F, 14, 18C, 19F, 20, 23F, and 25, may be purified as shown in U.S. Pat. No. 4,242,501.

Pneumococcal cultures of each type useful in this invention are stored and available worldwide from a great number of culture libraries. The American Type Culture Collection (ATCC), 12301 Parklawn Dr., Rockville, Md., U.S.A. 20852, lists all of the pneumococcal types of this invention as being freely available.

The 1978 ATCC catalogue designates these types as follows: (See Table I)

TABLE I

| Danish Type Nomenclature | U.S. Nomenclature | Catalogue Number |
|---|---|---|
| 1 | 1 | 6301 |
| 2 | 2 | 6302 |
| 3 | 3 | 6303 |
| 4 | 4 | 6304 |
| 5 | 5 | |
| 6A | 6 | 6306 |
| 6B | 26 | 6326 |
| 7F | 51 | 10351 |
| 8 | 8 | 6308 |
| 9N | 9 | 6309 |
| 9V | 68 | |
| 10A | 34 | |
| 11A | 43 | |
| 12F | 12 | 6312 |
| 14 | 14 | 6314 |
| 15B | 54 | |
| 17F | 17 | |
| 18C | 56 | 10356 |
| 19A | 57 | |
| 19F | 19 | 6319 |
| 20 | 20 | 6320 |
| 22F | 22 | |
| 23F | 23 | 6323 |
| 25 | 25 | 6325 |
| 33F | 70 | |

The critical step in the preparation of a vaccine is purification of the immunogenic material such that extraneous material is removed without loss of those properties of the retained material that will cause the appropriate antibody production. Such properties of polysaccharides appear to reside in the retention of what may be termed the "native state configuration" of the polysaccharides.

Among those materials to be separated from the polysaccharides are proteins, nucleic acids, and "C" polysaccharide. "C" polysaccharide is found in high concentration in Danish designation pneumococcal types 4, 7F and 14, and may be separated therefrom as shown in U.S. Pat. No. 4,242,501.

Nucleic acids (which absorb light at 260 MU) are difficult to reduce to a satisfactory level in preparations of pneumococcal polysaccharides. This problem is in contradistinction to the situation presented by meningococcal polysaccharide which is more easily purified while retaining immunogenicity. Meningococcal polysaccharide may be purified by relatively harsh methods as shown in U.S. Pat. No. 3,636,192 to Gotschlich. There are 85 specific types of pneumococcus. These types are designated by both American and Danish numbering systems. Type designations cited herein are to the Danish numbering. Each type appears to require a particular method for eliminating contaminants, but no single method is applicable to all types of pneumococcal polysaccharides. Further the specific proper method appears to be unpredictable. As exemplary of the different procedures used to purify various pneumococcal polysaccharides, some require a large quantity of ethanol for precipitation which can be partially separated from nucleic acids by fractional precipitation as the nucleic acids are precipitated in the lower alcohol ranges using 3A alcohol. 3A alcohol is 5% absolute methanol and 95% absolute ethanol. Absolute ethanol would behave in an essentially identical manner and is considered fully equivalent. Throughout this specification the term "alcohol" will designate 3A alcohol unless otherwise specified.

With other types, polysaccharides are precipitated in the 30–50% range, thus alcohol is not effective as a separatory precipitant. In contrast, other types can be separated from nucleic acids by carefully controlled amounts of protamine sulfate. With these types, at an optimal concentration of protamine sulfate (0.02–0.20%), nucleic acids are precipitated and can be pelleted by high speed centrifugation. However, any excess protamine sulfate in the system beyond the minimum amount required to precipitate the constituent nucleic acid will additionally precipitate the polysaccharide. An example of another type of purification of pneumococcal polysaccharide is presented by the purification often used for Type 3 pneumococcus, which is difficult to separate from nucleic acid. If calcium acetate is substituted for sodium acetate as the electrolyte in a solution of Type 3 pneumococcal polysaccharide, the polysaccharide can be precipitated with a minimal amount of alcohol (10–12%). However, this method sometimes allows substantial amounts of nucleic acid to remain soluble in the supernatant phase. The behavior of various pneumococcal polysaccharide types in a reaction of the polysaccharide-nucleic acid mixtures with ammonium sulfate is also variable. Some polysaccharides are precipitated by ammonium sulfate salt at 50–60% saturation whereas others are not. Type 1 polysaccharide is not precipitated with ammonium sulfate whereas Type 3 and Type 4 may be separated to some degree from nucleic acids by 50% saturation with ammonium sulfate. From the foregoing exposition and from the following references [Guy, R. C. W., How, J., Stacey, M., Heidelberger, M., J. Biol. Chem. 242: 21 (1967); Brown, R., J. Immunol. 37: 445 (1939); Glaudemans, C. P. J., Treffers, H. P., Carbohydrate Res. 4, (1967); Kabat, E. A., Exp. Immunochemistry, Charles C. Thomas, publisher, pp. 838–842 (1967)], it can be seen that there is no one satisfactory method for the removal of contaminants from pneumococcal polysaccharide applicable to all types in view of the fact that there are 85 or more types of pneumococcus and the production of a practical vaccine usually requires a multivalent vaccine comprising polysaccharide fractions from many species of pneumococcus, each retaining a relatively native state configuration.

Another contaminant of pneumococcal polysaccharide is protein. Although alcohol precipitation is effective in reducing the level of protein contamination, it is unable to reduce the contamination to a level satisfactory for a parenteral product. One method commonly employed to reduce the level of protein is to subject a mixture of pneumococcal polysaccharides and protein to organic solvents. For example, the "Sevag" procedure [Sevag, M. G. Biochem. Z., 272: 419 (1934)] involves extraction of chloroform and butanol mixtures shaken vigorously for 4-6 hours and then subjected to low speed centrifugation. Denatured protein which collects at the interface can then be separated from the aqueous phase with the polysaccharides. However, this procedure is unsatisfactory as the extraction often adversely affects the pneumococcal polysaccharides causing their breakdown, depolymerization or loss of native state configuration. The result is polysaccharides that are not effective as immunogens. Other procedures may be employed to reduce protein contamination such as ammonium sulfate precipitation and molecular sieving, but such procedures are specific to each group of proteins and peptides among the many different sizes and types of proteins in the solution. Here again the variability of the polysaccharides, depending on the strain, determines the effectiveness of the particular protein separatory step employed. Further, one may conclude that no one procedure is effective in purifying all pneumoccocal capsular polysaccharides, and prediction of the behavoir of a particular pneumococcal capsular polysaccharide appears impossible.

However, a number of methods of purifying pneumococcal capsular polysaccharides with high purity and retention of immunogenic properties have now been discovered. These purifications have been specifically directed to the purification of 10 types of pneumococcus. These types are 3, 5, 9V, 10A, 11A, 15B, 17F, 19A, 22F and 33F (Danish designation).

SUMMARY OF THE INVENTION

The subject of this invention is a multivalent vaccine of a combination of effective immunogenic amounts of the pneumococcal capsular polysaccharides from the group, by Danish designation, types 1, 2, 3, 4, 5, 6B, 7F, 8, 9N, 9V, 10A, 11A, 12F, 14, 15B, 17F, 18C, 19A, 19F, 20, 22F, 23F and 33F, and from none to one or both of 6A and 25, and substantially absent "C" polysaccharide, a major contaminant of types 4, 7F, and 14. As defined in this specification, substantially absent "C" polysaccharide refers to less than 0.5% "C" polysaccharide. Central to the preparation of this multivalent vaccine is the method of preparing the purified capsular polysaccharide of each of the 10 types used in this vaccine. After the pneumococcus bacteria have been grown by any suitable method of fermentation to stationary growth phase, the fermentation is stopped by the addition of an effective amount of sodium desoxycholate to lyse all bacterial cells and release cell-associated polysaccharide into the medium. Cellular debris is removed from the medium to be followed by one or two alcohol precipitations. This procedure removes a great deal of the contaminants including protein from the pneumococcal polysaccharides.

Carefully controlled alcohol precipitation is a major step in the present process in the purification of all the polysaccharides, with each polysaccharide being precipitated at least 5 times by alcohol. This avoids the more harsh chloroform-butanol extraction.

Two types of alcohol precipitation are used.

In the first, sufficient alcohol is added to the sample to precipitate the polysaccharides. The pellet is then separated from the supernatant by centrifugation and redissolved in distilled water.

The second type is a fractional alcohol precipitation. The maximum amount of alcohol is added which does not precipitate the polysaccharides. The pellet of contaminants is then removed by centrifugation and sufficient alcohol is then added to the supernatant to precipitate the polysaccharides. The polysaccharide pellet is then harvested by centrifugation and the polysaccharides are redissolved in the distilled water.

At the end of both types of precipitation, any particular matter undissolved in the water is not polysaccharide and is removed by centrifugation or filtration.

The hexadecyltrimethylammonium bromide (cetavlon) treatment of pneumococci follows several alcohol precipitations to be most effective, being an improvement over use at earlier stages in the purification procedure.

Cetavlon, with most of the pneumococcal types of the present invention, is a critical separatory step. In these types, this step under carefully controlled conditions serves either to precipitate the polysaccharide preferentially to protein and nucleic acid contaminants, or in the reverse, preferentially precipitating contaminants. Those polysaccharides that precipitate may then be solubilized, in sodium chloride (usually 0.25M) and centrifuged to remove contaminating macromolecules which are insoluble in the salt. Though the concentration of hexadecyltrimethylammonium bromide and salt may vary for optimal purification of the polysaccharide, this procedure has proven effective for types 3, 5, 11A, 15B, 17F and 22F which are precipitated.

Four types (9V, 19A, 23F and 33F) are not precipitated by hexadecyltrimethylammonium bromide. In the case of these four types, the hexadecyltrimethylammonium bromide is added and the resulting contaminant precipitate, separated by centrifugation, is discarded. Since hexadecyltrimethylammonium bromide is soluble in alcohol, subsequent alcohol precipitations are effective both in further purifying the polysaccharide and in removing residual hexadecyltrimethylammonium bromide. This general scheme is the broad procedure suitable with variations to a number of pneumococcal polysaccharide types. Type 10A is peculiar in that it is not purified through the use of cetavlon.

After the treatment with alcohol, which effectively removes the cetavlon, different steps may be incorporated for contaminants unique to specific strains. The pneumococcal polysaccharide can then be dialyzed, lyophilized, and stored as a dry powder at −20° C. or lower.

A vaccine can be made by dissolving the polysaccharides in an appropriate buffer, such as phosphate buffer, containing a preservative followed by sterile filtration.

A common purification scheme for a pneumococcal polysaccharide can be summarized as follows:

Culture lysed by desoxycholate

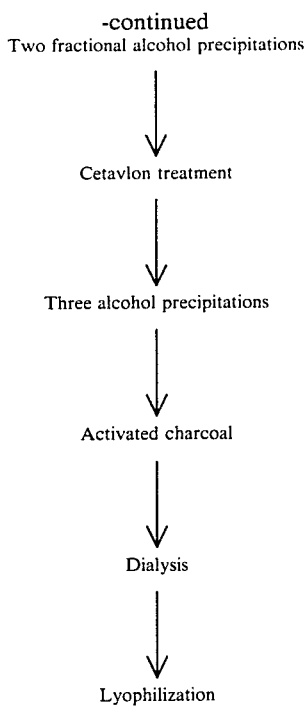

-continued
Two fractional alcohol precipitations
↓
Cetavlon treatment
↓
Three alcohol precipitations
↓
Activated charcoal
↓
Dialysis
↓
Lyophilization It is an object of this invention to provide a highly purified effectively immunogenic multivalent pneumococcal polysaccharide vaccine, substantially absent "C" polysaccharide contamination, for types 1, 2, 3, 4, 5, 6B, 7F, 8, 9N, 9V, 10A, 11A, 12F, 14, 15B, 17F, 18C, 19A, 19F, 20, 22F, 23F and 33F, and from none to one or both of 6A and 25 pneumococcus.

It is a particular object of this invention to provide a highly immunogenic pneumococcal polysaccharide vaccine, substantially absent "C" polysaccharide contamination, for types 1, 2, 3, 4, 5, 6B, 7F, 8, 9N, 9V, 10A, 11A, 12F, 14, 15B, 17F, 18C, 19A, 19F, 20, 22F, 23F and 33F, and from none to one or both of 6A and 25.

It is another object of the present invention to provide a process for purifying immunologically active capsular polysaccharides of types 3, 5, 9V, 10A, 11A, 15B, 17F, 19A, 22F and 33F pneumococcus.

DETAILED DESCRIPTION OF THE INVENTION

An effective multivalent pneumococcal vaccine absent "C" polysaccharide may be prepared by adding to a solution of 0.1M phosphate buffer containing 0.01% thimerosal sufficient lyophilized immunologically active pneumococcal polysaccharide to yield a final concentration of about 100 micrograms/ml/type. This is a generally effective amount as the exact concentration of a polysaccharide to provide immunity exhibits variance with both the pneumococcal type and subject to be immunized.

This mixture is stirred about 4 hours at about 4° C. and sterile filtered. In one embodiment 1.0 mg each of lyophilized pneumococcal polysaccharide of types 1, 2, 3, 4, 5, 6A, 6B, 7F, 8, 9N, 9V, 10A, 11A, 12F, 14, 15B, 17F, 18C, 19A, 19F, 20, 22F, 23F, 25 and 33F is combined with 0.1M phosphate buffer containing 0.01% thimerosal to a final volume of 10 cc and stirred for about 4 hours at 4° C. Types 4, 7F, and 14 are added in a state essentially free (less than 0.5% of "C" polysaccharide present) from "C" polysaccharide and exhibiting effective immunogenicity.

In the preferred embodiment, the above procedure is utilized, but only 23 pneumococcal types are used. These types are types 1, 2, 3, 4, 5, 6B, 7F, 8, 9N, 9V, 10A, 11A, 12F, 14, 15B, 17F, 18C, 19A, 19F, 20, 22F, 23F and 33F. Critical to the above preparations of an effective multivalent vaccine is the purification of each pneumococcal type utilized without loss of native state configuration and hence loss of effective immunogenicity. Of the ensuing examples, 10 will illustrate the specific methods of obtaining pure immunologically active polysaccharide from specific pneumococcus types. These types may be utilized for causing specific immunogenic response in warm-blooded animals or be utilized in combinations as multivalent vaccines. The two multivalent vaccines described above will be seen as merely illustrative of the many combinations of multivalent vaccines which may be prepared utilizing in whole or in part the 25 purified pneumococcal capsular polysaccharides of the present invention.

These examples are arranged in the following order:

| Examples | Danish Types | American Types |
| --- | --- | --- |
| 1 | 3 | 3 |
| 2 | 5 | 5 |
| 3 | 9V | 68 |
| 4 | 10A | 34 |
| 5 | 11A | 43 |
| 6 | 15B | 54 |
| 7 | 17F | 17 |
| 8 | 19A | 57 |
| 9 | 22F | 22 |
| 10 | 33F | 70 |

Pneumococcal types which by Danish designation are types 1, 2, 4, 8, 12F, 25, 6A, 6B, 7F, 9N, 14, 19F, 20, 23F and 18C may be prepared as set forth in U.S. Pat. No. 4,242,501, incorporated herein by reference thereto.

EXAMPLE 1

Type 3 Pneumococcus

PREPARATION OF RAW POLYSACCHARIDE SUSPENSION

Three to five hundred liters of medium is used to grow Type 3 pneumococcus under conditions suitable for such growth to reach stationary phase. The bacteria are then lysed by the addition of a 10% sterile filtered solution of suitable lysant, herein sodium desoxycholate. Many methods of lysing such as other detergents and mechanical methods such as sonic disruption and French pressure cells may be used. All would produce fully equivalent material for the process of this invention. When sodium desoxycholate is used, a suitable lysing concentration has been found to be about 0.1–0.2%. All bacterial cells are lysed releasing cell associated polysaccharide into the medium. The turbid medium is clarified by centrifugation. Herein a model 16 Sharples centrifuge was used at 16,000 rpm and at a flowrate of 36–40 liters per hour while maintaining a temperature of about 2°–10° C. Cellular debris thus collected is discarded. The polysaccharide bearing supernatant is adjusted to a pH of about 6.6. In these examples pH adjustment was usually accomplished by the addition 8M acetic acid. It is important to note that the exact pH values designated in the preliminary steps are general and indicative only of the preferred mode. Wide variance in the useful pH ranges is to be understood with all pneumococcal types. Only the precipitating steps utilizing cetavlon require a highly specific pH be observed. Similarly, acetic acid is merely illustrative of one acidifying agent. Acetic acid is preferred as permitting use of sodium acetate with an attendant buffering action, but those skilled in the art will immediately understand that other pH adjusting systems of other acids, bases, and buffers could easily be devised. The above prepares a raw polysaccharide supernatant for the purification process of this invention.

PURIFICATION OF THE POLYSACCHARIDE: TYPE 3

(A) First Alcohol Precipitation

To the raw polysaccharide supernatant sodium acetate is added to a final concentration of about 4% as against supernatant and alcohol. pH is adjusted to about 6.7 and in the preferred mode to ±0.1 with 8M acetic acid. Alcohol is added from 0.15 volumes to 0.5 volumes and preferably 0.25 volumes, slowly with stirring at a temperature of 2°–6° C. The pH is adjusted to about 7.0 and in the preferred mode to ±0.1 with 8M acetic acid. As the polysaccharide precipitate forms slowly, the mixture is permited to stand overnight, about 16–20 hours, and centrifuged. As pneumococcal polysaccharides tend to be labile, they are handled at reduced temperatures, thus during the 16–20 hour period the polysaccharide precipitate should be kept chilled, here about 4° C. The polysaccharide precipitate is dissolved with stirring in sufficient 4% sodium acetate solution, usually about 100 liters, reduced temperature, about 4° C. being preferred. Brief mechanical agitation in a blender (4 to 6 seconds) aids this dissolution. If turbidity is apparent, the solution may be clarified by filtration or centrifugation at a reduced temperature, about 2°–6° C., and at a flow rate of about 16–18 liters per hour.

(B) Second Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and ±0.1 as above being preferred. Alcohol from about 0.25 to 0.6 volumes is added, and in the preferred embodiment 0.4 volumes, the pH adjusted to 7 and treated as described in the first alcohol precipitation with stirring chilled, pH adjustment, standing and clarification through filtration or centrifugation. The polysaccharide precipitate thus removed, is redissolved in 50 liters of water and the water removed by lyophilization. The dry powder is redissolved in 200 liters of water and centrifuged to remove turbidity. The supernatant is filtered using a Niagra filter press loaded with CPX 10C and CPX 70C pads (AMF CUNO) or equivalent. The partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first alcohol precipitation and ±0.1 in the preferred embodiment and alcohol from about 0.1 to 0.5 volume is added to a final minimum concentration of 0.5 volumes in the preferred embodiment and the pH adjusted to 7. This is followed by standing, as in the first alcohol precipitation, centrifugation, and again being redissolved in about 200 liters of cold pyrogen-free water, about 4° C. in the preferred embodiment.

(C) Hexadecyltrimethylammonium Bromide (Cetavlon) Fraction Precipitation

The polysaccharide solution is then allowed to warm to room temperature (21°–25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 0.1 to 0.5 volumes percent with the preferred concentration being 0.3 volumes percent. After standing until the precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 3 pneumococcal polysaccharide is precipitated by cetavlon along with some impurities. THe precipitate is redissolved in 40 liters of about 0.25M sodium chloride and stirred chilled, here about 4° C. The turbid suspension is filtered or centrifuged chilled, here at a flow rate of about 6–7 liters per hour and at 7°–12° C. The polysaccharide is now in solution while the nucleic acid and other impurities are in the centrifugation pellet which may be discarded. This procedure removes most of the nucleic acid and protein impurities remaining after alcohol precipitation.

The polysaccharide is then reprecipitated, the supernatant being adjusted to a pH of about 6.6 and sodium acetate added to about 4%. The pH then raised to about 6.7 and about 0.50 volumes of alcohol is added, and the pH adjusted to 7 at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

Throughout this specification, concentrations of cetavlon will be expressed values % based on a 10% cetavlon solution. It is to be understood that altering the concentration of the cetavlon solution would correspondingly alter the amount of such solution added to reach an equivalent final concentration.

(D) Activated Charcoal Purification

The polysaccharide solution, still chilled, is then adjusted to a pH of about 6.1 with 0.3M acetic acid and sodium chloride to a 0.15M concentration. A 20% suspension of activated charcoal is added with stirring to result in a 3 to 7% concentration of activated charcoal with 5% being preferred. The mixture is permitted to stand chilled, about 4° C., for about 30 minutes. This mixture is filtered to remove activated charcoal and further clarified by passage through a series of cartridge and/or membrane filters. In the preferred embodiment, a CPX-10C (AMF-CUNO) filter pad was used, followed by 1.2, 0.65, 0.45 and 0.22u Millipore membranes. During this procedure, optical density at 260mu can be used as a check on nucleic acid concentration and the method of Lowry, et al. can be used to monitor protein content.

The resultant filtrate is warmed to room temperature, around 21°–25° C., prior to dialysis. Here a Model DC 30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 3. This powder is harvested under low humidity into jars which are then tightly sealed and stored super cold, below −20° C. being found suitable.

The above process has removed more than 99% of contaminant protein and nucleic acid while retaining the immunogenicity of the product.

Throughout the specification, concentrations of activated charcoal will be expressed in volumes percent based on a 20% activated charcoal suspension. It is to be understood that altering the concentration of such suspension would correspondingly alter the amount of such suspension needed to reach an equivalent final concentration.

EXAMPLE 2

Type 5 Pneumococcus

PREPARATION OF RAW POLYSACCHARIDE SUSPENSION

The raw polysaccharide is prepared from a type 5 fermentation broth lysate as in the manner described in Example 1 for Type 3.

PURIFICATION OF THE POLYSACCHARIDE: TYPE 5

(A) First Fractional Alcohol Precipitation

To the raw polysaccharide supernatant, sodium acetate is added to a final concentration of about 4% as against supernatant and alcohol. pH is adjusted to about 6.7 and in the preferred mode to ±0.1 with 8M acetic acid. Alcohol is added from 0.25 volumes to 0.8 volumes and preferably 0.5 volumes, slowly with stirring at a temperature of 2°–6° C. The pH is adjusted to about 7.0, and in the preferred mode to ±0.1 with 8M acetic acid. As the precipitate forms slowly the mixture is permitted to stand overnight, about 16–20 hours. As pneumococcal polysaccharides tend to be labile, they are best handled at reduced temperatures. Thus during the 16–20 hour period, the polysaccharide bearing solution should be kept chilled here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation at a flow rate of about 16–20 liters per hour while kept at a reduced temperature, the preferred temperature being from about 2° C. to about 6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For type 5, alcohol is added from about 0.9 volume to about 1.4 volumes minimum and the pH adjusted to 7. With type 5, the preferred final alcohol concentration must exceed about 1.25 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or by centrifugation at a reduced temperature, about 2°–6° C.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and ±0.1 as above being preferred. Alcohol from about 0.25 to 0.80 volumes is added, and in the preferred embodiment 0.5 volumes the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 0.9 to 1.4 volume is added to a final minimum concentration of 1.25 volumes in the preferred embodiment and the pH adjusted to 7. This is followed by standing, as in the first fractional alcohol precipitation, centrifugation, and again being redissolved in about 40 liters of cold pyrogen-free water, about 4° C. in the preferred embodiment.

(C) Hexadecyltrimethylammonium Bromide (Cetavlon) Fraction Precipitation

The polysaccharide solution is then allowed to warm to room temperature (21°–25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 1.0 to 5.0 volumes percent with the preferred concentration being 2.00 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure type 5 pneumococcal polysaccharide is precipitated by cetavlon along with some impurities. The precipitate is redissolved in 40 liters of about 0.25M sodium chloride and stirred chilled, here about 4° C. The turbid suspension is filtered or centrifuged chilled, here at a flow rate of about 6–7 liters per hour and at 7°–12° C. The polysaccharide is now in solution while the nucleic acid and other impurities are in the centrifugation pellet, which may be discarded. The procedure removes most of the nucleic acid and protein impurities remaining after alcohol fractionation.

The polysaccharide is then reprecipitated, the supernatant being adjusted to a pH of about 6.6 with sodium acetate to about 4%. The pH is then raised to about 6.7 and about 1.25 volumes of alcohol are added, the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to a pH of about 6.1 with 0.3M acetic acid and sodium chloride to a 0.15M concentration. A 20% suspension of activated charcoal is added with stirring to result in a 2% to 7% concentration of activated charcoal with 5% being preferred. The mixture is permitted to stand chilled, about 4° C., for about 30 minutes. This mixture is filtered to remove activated charcoal and further clarified by pasage through a series of filter pads or membranes. In the preferred embodiment, a CPX-10C (AMF-CUNO) filter pad was used followed by 1.2, 0.65, 0.45, and 0.22u Millipore (293 mm) membranes. During this procedure, optical density at 260mu is monitored as a check on nucleic acid concentration and the method of Lowry, et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of type 5. This powder is harvested under low humidity into jars which are then tightly sealed and stored super cold, below −20° C. being found suitable.

The above process has removed more than 90% of contaminant protein and 99% of contaminant nucleic acid while retaining the immunogenicity of the product.

EXAMPLE 3

Type 9V Pneumococcus

PREPARATION OF RAW POLYSACCHARIDE SUSPENSION

The raw polysaccharide is prepared from a Type 9V fermentation broth lysate as in the manner described in Example 1 for Type 3.

PURIFICATION OF THE POLYSACCHARIDE: TYPE 9V (A) First Fractional Alcohol Precipitation To the raw polysaccharide supernatant sodium acetate is added to a final concentration of about 4% as against supernatant and alcohol. The pH is adjusted to about 6.7 and in the preferred mode to ±0.1 with 8M acetic acid. Alcohol is added from 0.25 volumes to 0.8 volumes and preferably 0.5 volumes, slowly with stirring at a temperature of 2°-6° C. The pH is adjusted to about 7.0, and in the preferred mode to ±0.1 with 8M acetic acid. As the precipitate forms slowly the mixture is permitted to stand overnight, about 16-20 hours. As pneumococcal polysaccharides tend to be labile, they are best handled at reduced temperatures. Thus during the 16-20 hour period the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16-20 liters per hour while kept at a reduced temperature, the preferred temperature being from about 2°-6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 9V, alcohol is added from about 1.25 volumes to about 2.25 volumes minimum and the pH adjusted to 7. With Type 9V the preferred final alcohol concentration must exceed about 1.75 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or by centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and +0.1 as above being preferred. Alcohol from about 0.15 and 0.35 volumes is added, and in the preferred embodiment 0.25 volumes the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.25 to 2.25 volumes are added to a final minimum concentration of 1.75 volumes in the preferred embodiment and the pH adjusted to 7. This is followed by standing, as in the first fractional alcohol precipitation, centrifugation, and again being redissolved in about 40 liter of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°-25° C.) and the pH is adjusted to 7.4±0.1 with sodium carbonate in solution. A concentration of 0.4% sodium carbonate has been found to be convenient for this adjustment solution.

Sodium chloride to 0.15M is added and with stirring, a 10% solution of cetavlon is added slowly to a concentration of 0.05 to 1.0 volume percent with the preferred concentration being 0.2 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure, Type 9V pneumococcal polysaccharide is not precipitated by cetavlon. The precipitate is discarded. The polysaccharide is now in solution while the nucleic acid and other impurities are in the centrifugation pellet, which may be discarded. This procedure removes most of the nucleic acid and protein impurities remaining after alcohol fractionation.

The supernatant bearing the polysaccharide is then reprecipitated, the supernatant being adjusted to a pH of about 6.6 and sodium acetate added to about 4%. The pH is then raised to about 6.7 and about 1.75 volumes of alcohol are added and the pH adjusted to 7, standing about 4° C. for 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to a pH of about 6.1 with 0.3M acetic acid and sodium chloride to a 0.15M concentration. A 20% suspension of activated charcoal is added with stirring to result in a 2% to 6% concentration of activated charcoal with 3% being preferred. The mixture is permitted to stand chilled, about 4° C., for about 30 minutes. This mixture is filtered to remove activated charcoal and further clarified by passage through a series of filter pads or membranes. In the preferred embodiment, a CPX-10C (AMF-CUNO) filter pad was used followed by 1.2, 0.65, 0.45, and 0.22u Millipore (293mm) membranes. During this procedure, optical density at 260mu is monitored as a check on nucleic acid concentration and the method of Lowry, et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 9V. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 4

Type 10A Pneumococcus

Preparation of Raw Polysaccharide Suspension

The raw polysaccharide is prepared from a Type 10A fermentation broth lysate as in the manner described in Example 1 for Type 3.

Purification of the Polysaccharide: Type 10A (A) First Fractional Alcohol Precipitation To the raw polysaccharide supernatant sodium acetate is added to a final concentration of about 4% as against supernatant and alcohol. The pH is adjusted to about 6.7 and in the preferred mode to ±0.1 with 8M acetic acid. Alcohol is added from 0.25 volumes to 0.8 volumes and preferably 0.5 volumes, slowly with stirring at a temperature of 2°–6° C. The pH is adjusted to about 7.0, and in the preferred mode to ±0.1 with 8M acetic acid. As the precipitate forms slowly, the mixture is permitted to stand overnight, about 16–20 hours. As pneumococcal polysaccharides tend to be labile, they are best handled at reduced temperatures. Thus during the 16–20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16–20 liters per hour while kept at a reduced temperature, the preferred temperature being from about 2°14 6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 10A alcohol is added from about 1.0 volume to about 1.5 volumes minimum and the pH adjusted to 7. With Type 10A, the preferred final alcohol concentration must exceed about 1.50 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or by centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and +0.1 as above being preferred. Alcohol from about 0.25 to 0.8 volumes is added, and in the preferred embodiment, 0.5 volumes and the pH adjusted to 7 and treated as described in the first fractional alcohol precipitation with stirring chilled, pH adjustement, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.0 to 2.0 volumes are added to a final minimum concentration of 1.5 volumes in the preferred embodiment and the pH adjusted to 7. This is followed by standing, as in the first fractional alcohol precipitation, centrifugation, and again being redissolved in about 40 liters of cold pyrogen-free water, about 4° C. in the preferred embodiment.

The polysaccharide is then reprecipitated, the supernatant being adjusted to a pH of about 6.6 with sodium acetate to about 4%. The pH is then raised to about 6.7 and about 1.5 volumes of alcohol are added, the pH adjusted to 7 standing at about 4° C. 16–20 hours and centrifuging down the polysacchardie which is again redissolved in pyrogen-free water, about 20 liters being suitable.

(C) Activated Charcoal Purification

The polysaccharide solution still chilled is then adjusted to a pH of about 6.1 with 0.3M acetic acid and sodium chloride to a 0.15M concentration. A 20% suspension of activated charcoal is added with stirring to result in a 4% to 8% concentration of activated charcoal with 6% being preferred. The mixture is permitted to stand chilled, about 4° C., for about 30 minutes. This mixture is filtered to remove activated charcoal and further clarified by passage through a series of filter pads or membranes. In the preferred embodiment, a CPX-10C (AMF-CUNO) filter pad was used followed by 1.2, 0.65, 0.45, and 0.22u Millipore (293mm) membranes. During this procedure optical density at 260mu is monitored as a check on nucleic acid concentration and the method of Lowry, et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 10A. This powder is harvested under low humidity into jars which are then tightly sealed and stored super cold, below $-20°$ C. being found suitable.

The above process has removed more than 99% of contaminant nucleic acid and 90% of contaminant protein while retaining the immunogenicity of the product

EXAMPLE 5

Type 11A Pneumococcus

Preparation of Raw Polysaccharide Suspension

The raw polysaccharide is prepared from a Type 11A fermentation broth lysate as in the manner described in Example 1 for Type 3.

Purification of the Polysaccharide: Type 11A (A) First Fractional Alcohol Precipitation To the raw polysaccharide supernatant, sodium acetate is added to a final concentration of about 4% as against supernatant and alcohol. The pH is adjusted to about 6.7 and in the preferred mode to $\pm 0.1$ with 8M acetic acid. Alcohol is added from 0.75 volumes to 1.25 volumes and preferably 1.0 volume, slowly with stirring at a temperature of 2°–6° C. The pH is adjusted to about 7.0, and in the preferred mode to $\pm 0.1$ with 8M acetic acid. As the precipitate forms slowly, the mixture is permitted to stand overnight, about 16–20 hours. As pneumococcal polysaccharides tend to be labile, they are best handled at reduced temperatures, thus during the 16–20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16–20 liters per hour while kept at a reduced temperature, the preferred temperature being from about 2°–6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 11A alcohol is added from about 1.5 volumes to about 2.25 volumes minimum and the pH adjusted to 7. With Type 11A, the preferred final alcohol concentration must exceed about 2.0 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment $\pm 0.1$ being accomplished with 8M acetic acid. Sodium acetate is added to a final concentraton of about 4% and the pH adjusted to about 6.7 and $\pm 0.1$ as above being preferred. Alcohol from about 0.75 to 1.25 volumes is added, and in the preferred embodiment 1.00 volume the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment $\pm 0.1$. To fully precipitate the polysaccharide, sodium acetate is added to about a 4% final concentration and the pH adjusted to about 6.7 as described in the first fractional alcohol precipitation and $\pm 0.1$ in the preferred embodiment. Alcohol from about 1.50 to 2.25 volumes are added to a final minimum concentration of 2.00 volumes in the preferred embodiment and the pH adjusted to 7. This is followed by standing, as in the first fractional alcohol precipitation, centrifugation, and again being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°–25° C.) and the pH is adjusted to 7.4$\pm 0.1$ with sodium carbonate in solution. A concentration of 0.4% sodium carbonate has been found to be convenient for this adjustment solution.

With stirring, a 10% solution of cetavlon is added slowly to a concentration of 1.5 to 5.0 volumes percent with the preferred concentration being 3.0 volumes percent. After standing until the precipitate forms, here about 90 minutes, the mixture is rechilled to about 4° C. and the precipitate removed by centrifugation. A flow rate of 6–8 liters per hour and a temperature of 7°–14° C. is used in the preferred embodiment, but these ranges are general. With this procedure, Type 11A pneumococcal polysaccharide is precipitated by cetavlon along with some impurities. The precipitate is redissolved in 40 liters of about 0.25M sodium chloride and stirred chilled, here about 4° C. The turbid suspension is filtered or centrifuged chilled, here at a flow rate of about 6–7 liters per hour and at 7°–12° C. The polysaccharide is now in solution while the nucleic acid and other impurities are in the centrifugation pellet, which may be discarded. This procedure removes most of the nucleic acid and protein impurities remaining after alcohol fractionation.

The polysaccharide is then reprecipitated, the supernatant being adjusted to a pH of about 6.6 with sodium acetate to about 4%. The pH then raised to about 6.7 and about 2 volumes of alcohol are added, the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to pH of about 6.1 with 0.3M acetic acid and sodium chloride to a 0.15M concentration. A 20% suspension of activated charcoal is added with stirring to result in a 2% to 5% concentration of activated charcoal with 3% being preferred. The mixture is permitted to stand chilled, about 4° C., for about 30 minutes. The mixture is filtered to remove activated charcoal and further clarified by passage through a series of filter pads and membranes. In the preferred embodiment a CPX-10C (AMF-CUNO) filter pad was used followed by 1.2, 0.65, 0.45, and 0.22u Millipore (293mm) membranes. During this procedure optical density of 260mu is monitored as a check on nucleic acid concentration and the method of Lowry, et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized, leaving purified pneumococcal polysaccharide powder, herein of Type 11A. This powder is harvested under low humidity into jars which are then tightly sealed and stored super cold, below $-20°$ C. being found suitable.

The above process has removed more than 99% of contaminant protein and nucleic acid while retaining the immunogenicity of the product.

EXAMPLE 6

Type 15B Pneumococcus

Preparation of Raw Polysaccharide Suspension

The raw polysaccharide is prepared from a Type 15B fermentation broth lysate as in the manner described in Example 1 for type 3.

Purification of the Polysaccharide: Type 15B (A) First Fractional Alcohol Precipitation To the raw polysaccharide supernatant, sodium acetate is added to a final concentration of about 4% as against supernatant and alcohol the pH is adjusted to about 6.7 and in the preferred mode to ±0.1 with 8M acetic acid. Alcohol is added from 0.4 volume to 1.0 volume and preferably 0.75 volume, slowly with stirring at a temperature of 2°–6° C. The pH is adjusted to about 7.0 and in the preferred mode to ±0.1 with 8M acetic acid. As the precipitate forms slowly, the mixture is permitted to stand overnight, about 16–20 hours. As pneumococcal polysaccharides tend to be labile, they are best handled at reduced temperatures. Thus during the 16–20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16–20 liters per hour while kept at a reduced temperature, the preferred temperature being from about 2°–6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 15B alcohol is added from about 1.5 volumes to about 2.25 volumes minimum and the pH adjusted to 7. With Type 15B, the preferred final alcohol concentration must exceed about 1.75 volumes for total polysaccharide precipitation.

The mixture is then allowed to stand at a reduced temperature and for a comparable time as in the first alcohol fractional precipitation and is similarly centrifuged; however, this is the polysaccharide in this step. The polysaccharide precipitate is dissolved with stirring in sufficient water, usually about 40 liters, reduced temperature, about 4° C. being preferred. If turbidity is apparent, the solution may be clarified by filtration or centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and ±0.1 as above being preferred. Alcohol from about 0.4 to 1.0 volume is added, and in the preferred embodiment 0.75 volume the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 1.5 to 2.25 volumes are added to a final minimum concentration of 1.75 volumes in the preferred embodiment and the pH adjusted to 7. This is followed by standing, as in the first fractional alcohol precipitation, centrifugation, and again being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°–25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 2.0 to 5.0 volumes percent with the preferred concentration being 3.0 volumes percent. After standing until the precipitate forms, here about 90 minutes, the mixture is rechilled to about 4° C. and the precipitate removed by centrifugation. A flow rate of 6-8 liters per hour and a temperature of 7°-14° C. is used in the preferred embodiment, but these ranges are general. With this procedure, Type 15B pneumococcal polysaccharide is precipitated by cetavlon along with some impurities. The precipitate is redissolved in 40 liters of about 0.25M sodium chloride and stirred chilled, here about 4° C. The turbid suspension is centrifuged chilled, here at a flow rate of about 6-7 liters per hour and at 7°-20° C. The polysaccharide is now in solution while the nucleic acid and other impurities are in the centrifugation pellet, which may be discarded. This procedure removes most of the nucleic acid and protein impurities remaining after alcohol fractionation.

The polysaccharide is then reprecipitated, the supernatant being adjusted to a pH of about 6.6 with sodium acetate to about 4%. The pH then raised to about 6.7 and about 1.75 volumes of alcohol are added, the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water. If turbidity is apparent, the solution may be clarified by filtration or centrifugation at a reduced temperature, about 2°-6° C. and at a flow rate of about 6-7 liters per hour.

(D) Diafiltration and Drying

The polysaccharide solution is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 15B. This powder is harvested under low humidity into jars which are then tightly sealed and stored super cold, below −20° C. being found suitable.

The above process has removed more than 98% of contaminant protein and 99% of contaminant nucleic acid while retaining the immunogenicity of the product.

EXAMPLE 7

Type 17F Pneumococcus

Preparation of Raw Polysaccharide Suspension

The raw polysaccharide is prepared from a Type 17F fermentation broth lysate as in the manner described in Example 1 for Type 3.

Purification of the Polysaccharide: Type 17F (A) First Fractional Alcohol Precipitation To the raw polysaccharide supernatant, sodium acetate is added to a final concentration of about 4% as against supernatant and alcohol. The pH is adjusted to about 6.7 and in the preferred mode to ±0.1 with 8M acetic acid. Alcohol is added from 0.25 volume to 0.75 volume and preferably 0.5 volume, slowly with stirring at a temperature of 2°-6° C. The pH is adjusted to about 7.0, and in the preferred mode to ±0.1 with 8M acetic acid. As the precipitate forms slowly, the mixture is permitted to stand overnight, about 16-20 hours at about 4° C. As pneumococcal polysaccharides tend to be labile, they are best handled at reduced temperatures. Thus during the 16-20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16-20 liters per hour while kept at a reduced temperature, the preferred temperature being from about 2°-6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 17F alcohol is added from about 1.0 volumes to about 1.5 volumes minimum and the pH adjusted to 7. With Type 17F, the preferred final alcohol concentration must exceed about 1.25 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or centrifugation at a reduced temperature about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and +0.1 as above being preferred. Alcohol from about 0.25 to 0.75 volume is added, and in the preferred embodiment 0.50 volume the pH adjusted to 7 and treated as described in the first fractional alcohol precipitation with stirring, chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 1.0 to 1.5 volumes are added to a final minimum concentration of 1.25 volumes in the preferred embodiment and the pH adjusted to 7. This is followed by standing, as in the first fractional alcohol precipitation, centrifugation, and again being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°-25° C.) and the pH is adjusted to 7.4+0.1 with sodium carbonate in solution. A concentration of 0.4% sodium carbonate has been found to be convenient for this adjustment solution.

With stirring, a 10% solution of cetavlon is added slowly to a concentration of 2.0 to 5.0 volumes percent with the preferred concentration being 3.0 volumes percent. After standing until the precipitate forms, here about 90 minutes, the mixture is rechilled to about 4° C. and the precipitate removed by centrifugation. A flow rate of 6-8 liters per hour and a temperature of 7°-14° C. is used in the preferred embodiment, but these ranges are general. With this procedure, Type 17F pneumococcal polysaccharide is precipitated by cetavlon along with some impurities. The precipitate is redissolved in 40 liters of about 0.25M sodium chloride and stirred chilled, here about 4° C. The turbid suspension is centrifuged chilled, here at a flow rate of about 6-7 liters per hour and at 7°-12° C. The polysaccharide is now in solution while the nucleic acid and other impurities are in the centrifugation pellet, which may be discarded. This procedure removes most of the nucleic acid and protein impurities remaining after alcohol fractionation.

The polysaccharide is then reprecipitated, the supernatant being adjusted to a pH of about 6.6 with sodium acetate to about 4%. The pH then raised to about 6.7 and about 1.25 volumes of alcohol are added, the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water (D) Activated Charcoal Purification The polysaccharide solution still chilled is then adjusted to a pH of about 6.1 with 0.3M acetic acid and sodium chloride to a 0.15M concentration. A 20% suspension of activated charcoal is added with stirring to result in a 3% to 6% concentration of activated charcoal with 4% being preferred. The mixture is permitted to stand chilled, about 4° C., for about 30 minutes. This mixture is filtered to remove activated charcoal and further clarified by passage through a series of filter pads and membranes. In the preferred embodiment, a CPX-10C (AMF-CUNO) filter pad was used followed by 1.2, 0.65, 0.45, and 0.22u Millipore membranes. During this procedure, optical density at 260mu is monitored as a check on nucleic acid concentration and the method of Lowry, et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 17F. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 8

Type 19A Pneumococcus

Preparation of Raw Polysaccharide Suspension

The raw polysaccharide is prepared from a Type 19A fermentation broth lysate as in the manner described in Example 1 for Type 3.

Purification of the Polysaccharide: Type 19A (A) First Fractional Alcohol Precipitation To the raw polysaccharide supernatant, sodium acetate is added to a final concentration of about 4% as against supernatant and alcohol. The pH is adjusted to about 6.7 and in the preferred mode to ±0.1 with 8M acetic acid. Alcohol is added from 0.5 volume to 1.0 volume and preferably 0.75 volume, slowly with stirring at a temperature of 2°-6° C. The pH is adjusted to about 7.0, and in the preferred mode to +0.1 with 8M acetic acid. As the precipitate forms slowly, the mixture is permitted to stand overnight, about 16-20 hours. As pneumococcal polysaccharides tend to be labile, they are best handled at reduced temperatures. Thus during the 16-20 hour period, 20 the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16-20 liters per hour while kept at a reduced temperature, the preferred temperature being from about 2°-6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 19A alcohol is added from about 1.5 volumes to about 2.0 volumes minimum and the pH adjusted to 7. With Type 19A, the preferred final alcohol concentration must exceed about 1.75 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and +0.1 as above being preferred. Alcohol from about 0.75 to 1.25 volumes is added, and in the preferred embodiment 1.0 volume the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 1.5 to 2.0 volumes are added to a final minimum concentration of 1.75 volumes in the preferred embodiment and the pH adjusted to 7. This is followed by standing, as in the first fractional alcohol precipitation, centrifugation, and again being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°-25° C.) and the pH is adjusted to 7.4±0.1 with sodium carbonate in solution. A concentration of 0.4% sodium carbonate has been found to be convenient for this adjustment solution.

Sodium chloride to 0.15M is added with stirring, a 10% solution of cetavlon is added slowly to a concentration of 0.05 to 0.2 volumes percent with the preferred concentration being 0.075 volumes percent. After standing until the precipitate forms, here about 90 minutes, the mixture is rechilled to about 4° C. and the precipitate removed by centrifugation. A flow rate of 6-8 liters per hour and a temperature of 7°-14° C. is used in the preferred embodiment, but these ranges are general. With this procedure, Type 19A pneumococcal polysaccharide is not precipitated by cetavlon. The precipitate is discarded. The polysaccharide is now in solution while the nucleic acid and other impurities are in the centrifugation pellet, which may be discarded. This procedure removes most of the nucleic acid and protein impurities remaining after alcohol fractionation.

The supernatant bearing the polysaccharide is then reprecipitated, the supernatant being adjusted to a pH of about 6.6 with sodium acetate to about 4%. The pH then raised to about 6.7 and about 1.75 volumes of alcohol are added, the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to a pH of about 6.1 with 0.3M acetic acid and sodium chloride to a 0.15M concentration. A 20% suspension of activated charcoal is added with stirring to result in a 5% to 9% concentration of activated charcoal with 7% being preferred. The mixture is permitted to stand chilled, about 4° C., for about 30 minutes. This mixture is filtered to remove activated charcoal and further clarified by passage through a series of filter pads and membranes. In the preferred embodiment, a CPX-10C (AMF-CUNO) filter pad was used followed by 1.2, 0.65, 0.45, and 0.22u Millipore membranes. During this procedure, optical density at 260mu is monitored as a check on nucleic acid concentration and the method of Lowry, et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 19A. Prior to lyophilization, 0.01% to 25% glycine is added to the diafiltrate with 0.2% as the preferred amount. This powder is harvested under low humidity into jars which are then tightly sealed and stored super cold, below −20° C. being found suitable.

The above process has removed more than 99% of contaminant protein and nucleic acid while retaining the immunogenicity of the product.

Example 9

Type 22F Pneumococcus

Preparation of Raw Polysaccharide Suspension

The raw polysaccharide is prepared from a Type 22F fermentation broth lysate as in the manner described in Example 1 for Type 3.

Purification of the Polysaccharide: Type 22F (A) First Fractional Alcohol Precipitation To the raw polysaccharide supernatant, sodium acetate is added to a final concentration of about 4% as against supernatant and alcohol. The pH is adjusted to about 6.7 and in the preferred mode to ±0.1 with 8M acetic acid. Alcohol is added from 0.25 volumes to 0.75 volumes and preferably 0.5 volumes, slowly with stirring at a temperature of 2°-6° C. The pH is adjusted to about 7.0, and in the preferred mode to ±0.1 with 8M acetic acid. As the precipitate forms slowly, the mixture is permitted to stand overnight, about 16-20 hours. As pneumococcal polysaccharides tend to be labile, they are best handled at reduced temperatures, thus during the 16-20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16-20 liters per hour wile kept at a reduced temperature, the preferred temperature being from about 2°-6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 22F alcohol is added from about 1.25 volumes to about 1.75 volumes minimum and the pH adjusted to 7. With Type 22F, the preferred final alcohol concentration must exceed about 1.50 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by filtration or centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8M acetic acid. Sodium acetate is added to a final concentration of about 4% and the pH adjusted to about 6.7 and ±0.1 as above being preferred. Alcohol from about 0.25 to 0.75 volumes are added, and in the preferred embodiment 0.50 volumes the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 1.25 to 1.75 volumes are added to a final minimum concentration of 1.50 volumes in the preferred embodiment and the pH adjusted to 7. This is followed by standing, as in the first fractional alcohol precipitation, centrifugation, and again being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°-25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 2.0 to 5.0 volumes percent with the preferred concentration being 3.0 volumes percent. After standing until the precipitate forms, here about 90 minutes, the mixture is rechilled to about 4° C. and the precipitate removed by centrifugation. A flow rate of 6-8 liters per hour and a temperature of 7°-14° C. is used in the preferred embodiment, but these ranges are general. With this procedure, Type 22F pneumococcal polysaccharide is precipitated by cetavlon along with some impurities. The precipitate is redissolved in 40 liters of about 0.25M NaCl and stirred chilled, here about 4° C. The turbid suspension is centrifuged chilled, here at a flow rate of about 6-7 liters per hours and at 7°-12° C. The polysaccharide is now in solution while the nucleic acid and other impurities are in the centrifugation pellet, which may be discarded. This procedure removes most of the nucleic acid and protein impurities remaining after alcohol fractionation.

The polysaccharide is then reprecipitated, the supernatant being adjusted to a pH of about 6.6 with sodium acetate to about 4%. The pH then raised to about 6.7 and about 1.5 volumes of alcohol are added, the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to a pH of about 6.1 with .3M acetic acid and sodium chloride to a 0.15M concentration. A 20% suspension of activated charcoal is added with stirring to result in a 3% to 7% concentration of activated charcoal with 5% being preferred. The mixture is permitted to stand chilled, about 4° C., for about 30 minutes. This mixture is filtered to remove activated charcoal and further clarified by passage through a series of filter pads and membranes. In the preferred embodiment, a CPX-10C (AMF-CUNO) filter pad was used followed by 1.2, 0.65, 0.45, and 0.22u Millipore membranes. During this procedure, optical density at 260mu is monitored as a check on nucleic acid concentration and the method of Lowry, et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 22F. This powder is harvested under low humidity into jars which are then tightly sealed and stored super cold, below −20° C. being found suitable.

The above process has removed more than 99% of contaminant protein and nucleic acid while retaining the immunogenicity of the product.

Example 10

Type 33F Pneumococcus

Preparation of Raw Polysaccharide Suspension

The raw polysaccharide is prepared from a Type 33F fermentation broth lysate as in the manner described in Example 1 for Type 3.

Purification of the Polysaccharide: Type 33F (A) First Fractional Alcohol Precipitation To the raw polysaccharide supernatant, sodium acetate is added to a final concentration of about 4% as against supernatant and alcohol. The pH is adjusted to about 6.7 and in the preferred mode to ±0.1 with 8M acetic acid. Alcohol is added from 0.25 volumes to 0.75 volumes, preferably 0.5 volumes, slowly with stirring at a temperature of 2°-6° C. The pH is adjusted to about 7.0, and in the preferred mode to ±0.1 with 8M acetic acid. As the precipitate forms slowly, the mixture is permitted to stand overnight, about 16-20 hours. As pneumococcal polysaccharides tend to be labile, they are best handled at reduced temperatures. Thus during the 16-20 hour period, the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the Sharples centrifuge at 16,000 rpm and a flow rate of about 16-20 liters per hour while kept at a reduced temperature, the preferred temperature being from about 2°-6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 33F alcohol is added from about 1.25 volumes to about 1.75 volumes minimum and the pH adjusted to 7. With Type 33F, the preferred final alcohol concentration must exceed about 1.50 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, at a reduced temperature, preferably about 4° C. being preferred. If turbidity is apparent, the solution may be clarified by filtration or centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and, in the preferred embodiment ±0.1, being accomplished with 8M acetic acid. Sodium acetate is added to a final concentration of about 4% and the pH adjusted to about 6.7 and +0.1 as above being preferred. Alcohol from about 0.25 to 0.75 volumes is added, and in the preferred embodiment 0.50 volume, the pH adjusted to 7 and treated as described in the first fractional alcohol precipitation with stirring, chilled, pH adjustment, standing and clarification through centrifugation. The precipitate is discarded, the partially purified polysaccharide supernatant fluid is adjusted to a pH of about 6.6 and in the preferred embodiment ±0.1. To fully precipitate the polysaccharide, sodium acetate is added to about a 4% final concentration and the pH adjusted to about 6.7 as described in the first fractional alcohol precipitation and ±0.1 in the preferred embodiment. Alcohol from about 1.25 to 1.75 volumes are added to a final minimum concentration of 1.50 volumes in the preferred embodiment and the pH adjusted to 7. This is followed by standing, as in the first fractional alcohol precipitation, centrifugation, and again the precipitate being redissolved in about 40 liters of cold, pyrogen-free water, about 4° C. in the preferred embodiment.

(C) Hexadecyltrimethylammonium Bromide (Cetavlon) Fractional Precipitation

The polysaccharide solution is then allowed to warm to room temperature (21°–25° C.) and the pH is adjusted to 7.4+0.1 with sodium carbonate in solution. A concentration of 0.4% sodium carbonate has been found to be convenient for this adjustment solution.

Sodium chloride is added to 0.15M with stirring, a 10% solution of cetavlon is added slowly to a concentration of 1.0 to 5.0 volumes percent, with the preferred concentration being 3.0 volumes percent. After standing until the precipitate forms, here about 90 minutes, the mixture is rechilled to about 4° C. and the precipitate removed by centrifugation. A flow rate of 6–8 liters per hour and a temperature of 7°–14° C. is used in the preferred embodiment, but these ranges are general. With this procedure, Type 33F pneumococcal polysaccharide is not precipitated by cetavlon. The precipitate is discarded. The polysaccharide is now in solution while the nucleic acid and other impurities are in the centrifugation pellet, which may be discarded. This procedure removes most of the nucleic acid and protein impurities remaining after alcohol fractionation.

The supernatant bearing the polysaccharide is then reprecipitated, the supernatant being adjusted to a pH of about 6.6 with sodium acetate to about 4%. The pH is then raised to about 6.7 and about 1.5 volumes of alcohol are added, the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution still chilled is then adjusted to a pH of about 6.1 with 0.3M acetic acid and sodium chloride to a 0.15M concentration. A 20% suspension of activated charcoal is added with stirring to result in a 3% to 7% concentration of activated charcoal with 4.5% being preferred. The mixture is permitted to stand chilled, about 4° C., for about 30 minutes. This mixture is filtered to remove activated charcoal and further clarified by passage through a series of filter pads and membranes. In the preferred embodiment, a CPX-10C (AMF-CUNO) filter pad was used followed by 1.2, 0.65, 0.45, and 0.22 u Millipore membranes. During this procedure, optical density at 260 mu is monitored as a check on nucleic acid concentration and the method of Lowry, et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized to obtain purified pneumococcal polysaccharide powder, herein of Type 33F. This powder is harvested under low humidity into jars which are then tightly sealed and stored super cold, below −20° C. being found suitable.

The above process has removed more than 97% of contaminant protein and 99% of contaminant nucleic acid while retaining the immunogenicity of the product.

We claim:

1. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 3 pneumococcal polysaccharide is purified from a clarified fermentation lysate by the process of
 (a) precipitating with 0.15 and 0.5 volumes of alcohol, the lysate being at a pH of about 6.7 and having a final sodium acetate concentration of about 4% and being at a temperature of 2°–6° C., and
 (b) redissolving such precipitate, and
 (c) repeating Step (a) at about 0.25 to 0.6 volumes of alcohol, and
 (d) repeating Step (b), and
 (e) repeating Step (a) with 0.1 to 0.5 volumes of alcohol, and
 (f) repeating Step (b), and
 (g) fractionally precipitating impurities from the polysaccharide of (f) with hexadecyltrimethylammonium bromide at a temperature of from 21°–25° C. and a pH of 7.4±0.1, and a hexadecyltrimethylammonium bromide concentration of 0.1 to 0.5 volumes percent based on a 10% hexadecyltrimethylammonium bromide solution, and
(h) reprecipitating the polysaccharide at a pH of about 6.7 with about 4% sodium acetate and about a 0.50 volume of alcohol, and redissolving in pyrogen-free water, and
(i) repeating Step (h) 2 times, and
(j) purifying the polysaccharide solution of (i) with activated charcoal at a pH of 6.1 and a sodium chloride concentration of 0.15M, by adding activated charcoal in suspension to a concentration of from 3% to 7% based on a 20% activated charcoal suspension, and the solution standing chilled for about 30 minutes and filtering out said activated charcoal, and
(k) diafiltering the solution against distilled water, and
(l) freezing and lyophilizing the resultant product.

2. In a multivalent pneumococcal vaccine comprising effective amounts of innumologically active purified pneumococcal capsular polysaccharide (substantially absent "C" polysaccharide) of pneumococcal types (Danish designation consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 5 pneumococcal polysaccharide is purified from a clarified fermentation lysate by the process of
(a) fractionally precipitating with 0.25 to 0.8 volumes of alcohol, the lysate being at a pH of about 6.7 and having a final sodium acetate concentration of about 4% and being at a temperature of 2°-6° C., and removing contaminants so precipitated, and
(b) precipitating Type 5 polysaccharide with from about 0.9 to about 1.4 volumes of alcohol at a pH of about 6.7, and
(c) collecting and redissolving such precipitate, and
(d) repeating Step (a) at about 0.25 to 0.80 volumes of alcohol, and
(e) repeating Step (b) and at 0.9 to 1.4 volumes of alcohol and then repeating step (c), and
(f) fractionally precipitating the redissolved precipitate of (e) with hexadecyltrimethylammonium bromide at a temperature of from 21°-25° C. and a pH of 7.4±0.1, and a hexadecyltrimethylammonium bromide concentration of 1.0 to 5.0 volumes percent, and based on a 10% hexadecyltrimethylammonium bromide solution, and
(g) removing the precipitated polysaccharide and redissolving the polysaccharide in about 0.25M sodium chloride while chilled, and
(h) reprecipitating the polysaccharide at a pH of about 6.7 with about 4% sodium acetate and about 1.25 volumes of alcohol, and redissolving in pyrogen-free water, and
(i) repeating Step (h) 2 times, and
(j) purifying the polysaccharide solution of (i) with activated charcoal at a pH of 6.1 and a sodium chloride concentration of 0.15M by adding activated charcoal in suspension to a concentration of from 2% to 7% based on a 20% activated charcoal suspension and the solution standing chilled for about 30 minutes and filtering out said activated charcoal, and
(k) diafiltering the solution against distilled water, and
(l) freezing and lyophilizing the resultant product.

3. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 9V pneumococcal polysaccharide is purified from a clarified fermentation lysate by the process of
(a) fractionally precipitating with 0.25 to 0.8 volumes of alcohol, the lysate being at a pH of about 6.7 and having a final sodium acetate concentration of about 4% being at a temperature of 2°-6° C., and removing contaminants so precipitated, and
(b) precipitating Type 9V polysaccharide with from about 1.25 to about 2.25 volumes of alcohol at a pH pf about 6.7, and
(c) collecting and redissolving such precipitate, and
(d) repeating Step (a) at about 0.15 to 0.35 volumes of alcohol, and
(e) repeating Step (b) and repeating Step (c), and·
(f) fractionally precipitating impurities from the polysaccharide of (e) with hexadecyltrimethylammonium bromide at a temperature of from 21°-25° C. and 0.15M sodium chloride and a pH of 7.4±0.1, and a hexadecyltrimethylammonium bromide concentration of 0.05 to 1.0 volumes percent based on a 10% hexadecyltrimethylammonium bromide solution, and
(g) reprecipitating the polysaccharide at a pH of about 6.7 with about 4% sodium acetate and about 1.75 volumes of alcohol, and redissolving in pyrogen-free water, and
(h) repeating Step (g) 2 times, and
(i) purifying the polysaccharide solution of (h) with activated charcoal at a pH of 6.1 and a sodium chloride concentration of 0.15M, by adding activated charcoal in suspension to a concentration of from 2% to 6% based on a 20% activated charcoal suspension and the solution standing chilled for about 30 minutes and filtering out said activated charcoal, and
(j) diafiltering the solution against distilled water, and
(k) freezing and lyophilizing the resultant product.

4. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 10A pneumococcal polysaccharide is purified from a clarified fermentation lysate by the process of
(a) fractionally precipitating with 0.25 to 0.8 volumes of alcohol, the lysate being at pH of about 6.7 and having a final sodium acetate concentration of about 4% and being at a temperature of 2°-6° C., and removing contaminants so precipitated and
(b) precipitating Type 10A polysaccharide with from about 1.0 to about 1.5 volumes of alcohol at a pH of about 6.7, and
(c) collecting and redissolving such precipitate, and
(d) repeating Step (a) at about 0.25 to 0.8 volumes of alcohol, and (e) repeating Step (b) at about 1.0 to 2.0 volumes of alcohol and repeating Step (c), and
(f) repeating Step (e), and
(g) purifying the polysaccharide solution of (f) with activated charcoal at a pH of 6.1 and a sodium chloride concentration of 0.15M, by adding activated charcoal in suspension to concentration of from 4% to 8% based on a 20% activated charcoal suspension, and the solution standing chilled for about 30 minutes and filtering out said activated charcoal, and
(h) diafiltering the solution against distilled water, and
(i) freezing and lyophilizing the resultant product.

5. In a multivalent pneumococcal vaccine comprising effective amounts of immunologically active purified pneucococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 11A pneumococcal polysaccharide is purified from a clarified fermentation lysate by the process of
(a) fractionally precipitating with 0.75 to 1.25 volumes of alcohol, the lystate being at a pH of about 6.7 and having a final sodium acetate concentration of about 4% and being at a temperature of 2°–6° C., and removing contaminants so precipitated, and
(b) precipitating Type 11A polysaccharide with from about 1.50 to about 2.25 volume of alcohol at a pH of about 6.7, and
(c) collecting and redissolving such precipitate, and
(d) repeating Step (a) at about 0.75 to 1.25 volumes of alcohol, and
(e) repeating Step (b) and at 1.50 to 2.25 volumes of alcohol and then repeating Step (c), and
(f) fractionally precipitating the redissolved precipitate of (e) with hexadecyltrimethylammonium bromide at a temperature of from 21°–25° C. and a pH of 7.4±0.1, and a hexadecyltrimethylammonium bromide concentration of 1.5 to 5.0 volumes percent based on a 10% hexadecyltrimethylammonium bromide solution, and
(g) removing the precipitated polysaccharide and redissolving the polysaccharide in about 0.25M sodium cholride while chilled, and
(h) reprecipitating the polysaccharide at a pH of about 6.7 with about 4% sodium acetate and about 2.0 volumes of alcohol, and redissolving in pyrogen-free water, and
(i) repeating Step (h) 2 times, and
(j) purifying the polysaccharide solution of (i) with activated charcoal at a pH of 6.1 and a sodium chloride concentration of 0.15M by adding activated charcoal in suspension to a concentration of from 2% to 5% based on a 20% activated charcoal suspension and the solution standing chilled for about 30 minutes and filtering out said activated charcoal, and
(k) diafiltering the solution against distilled water, and
(l) freezing and lyophilizing the resultant product.

6. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 15B pneumococcal polysaccharide is purified from a clarified fermentation lysate by the process of
(a) fractionally precipitating with 0.4 to 1.0 volumes of alcohol, the lysate being at a pH of about 6.7 and having a final sodium acetate concentration of about 4% and being at a temperature of 2°–6° C., and removing contaminants so precipitated, and
(b) precipitating Type 15B polysaccharide with from about 1.50 to about 2.25 volumes of alcohol, and
(c) collecting and redissolving such precipitated, and
(d) repeating Step (a) at about 0.4 to 1.0 volumes of alcohol, and
(e) repeating Step (b) and them repeating Step (c), and
(f) fractionally precipitating the dissolved polysaccharide fraction of (e) with hexadecyltrimethylammonium bromide at a temperature of from 21°–25° C. and a pH of 7.4±0.1, and a hexadecyltrimethylammonium bromide concentration of 2.0 to 5.0 volumes percent based on a 10% hexadecyltrimethylammonium bromide solution, and
(g) removing the precipitated polysaccharide and redissolving the polysaccharide in about 0.25M sodium chloride while chilled, and
(h) reprecipitating the polysaccharide at a pH of about 6.7 with about 4% sodium acetate and about 1.75 volumes of alcohol, and redissolving in pyrogen-free water, and
(i) repeating Step (h) 2 times, and
(j) diafiltering the solution against distilled water, and
(k) freezing and lyophilizing the resultant product.

7. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 17F pneumococcal polysaccharide is purified from a clarified fermentation lysate by the process of
(a) fractionally precipitating with 0.25 to 0.75 volumes of alcohol, the lystate being at a pH of about 6.7 and having a final sodium acetate concentration of about 4% and being at a temperature of 2°–6° C., and removing contaminants so precipitated, and
(b) precipitating Type 17F polysaccharide with from about 1.0 to about 1.5 volumes of alcohol at a pH of about 6.7, and
(c) collecting and redissolving such precipitate, and
(d) repeating Step (a) at about 0.25 to 0.75 volumes of alcohol, and
(e) repeating Step (b) at about 1.0 to 1.5 volumes of alcohol and repeating Step (c), and
(f) fractionally precipitating the redissolved precipitate of (e) with hexadecyltrimethylammonium bromide at a temperature of from 21°–25° C. and a pH of 7.4±0.1, and a hexadecyltrimethylammonium bromide concentration of 2.0 to 5.0 volumes percent, based on a 10% hexadecyltrimethylammonium bromide solution, and (g) removing the precipitated polysaccharide and redissolving the polysaccharide in about 0.25M sodium chloride while chilled, and (h) reprecipitating the polysaccharide at a pH of about 6.7 with about 4% sodium acetate and about 1.25 volumes of alcohol, and redissolving in pyrogen-free water, and (i) repeating Step (h) 2 times, and (j) purifying the polysaccharide solution of (i) with activated charcoal at a pH of 6.1 and a sodium chloride concentration of 0.15M, by adding activated charcoal in suspension to a concentration of from 3.0% to 6.0% based on a 20% activated charcoal suspension, and the solution standing chilled for about 30 minutes and filtering out said activated charcoal, and (k) diafiltering the solution against distilled water, and (l) freezing and lyophilizing and resultant product.

8. In a multivalent pneumococcal vaccine comprising effective amounts of immunologically active purified pneumococcal capsular polysaccharide (substantially absent "C" polysaccharide) of pneumococcal types (Danish designation)consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 19A pneumococcal polysaccharide is purified from a clarified fermentation lysate by to process of (a) fractionally precipitating with 0.5 to 1.0 volumes of alcohol, the lysate being at a pH of about 6.7 and having a final sodium acetate concentration of about 4% and being at a temperature of 2°-6° C., and removing contaminants so precipitated, and (b) precipitating Type 19A polysaccharide with from about 1.5 to about 2.0 volumes of alcohol at a pH of about 6.7, and (c) collecting and redissolving such precipitate, and (d) repeating Step (a) at about 0.75 to 1.25 volumes of alcohol, and (e) repeating Step (b) and repeating Step (c), and (f) fractionally precipitating impurities from the polysaccharide of (e) with hexadecyltrimethylammonium bromide at a temperature of from 21°-25° C. and 0.15M sodium chloride and a pH of 7.4±0.1, and a hexadecyltrimethylammonium bromide concentration of 0.05 to 0.2 volumes percent based on a 10% hexadecyltrimethylammonium bromide soltion, and (g) reprecipitating the polysaccharide at a pH of about 6.7 with about 4% acetate and about 1.75 volumes of alcohol, and redissolving in pyrogen-free water, and (h) repeating Step (g) 2 times, and (i) purifying the polysaccharide solution of (h) with activated charcoal at a pH of 6.1 and a sodium chloride concentration of 0.15M by adding activated charcoal in suspension to a concentration of from 5% to 9% based on a 20% activated charcoal suspension and the solution standing chilled for about 30 minutes and filtering out said activated charcoal, and (j) diafiltering the solution against distilled water, and (k) adding 0.01 to 25% glycine to the filtrate, and (l) freezing and lyophilizing the resultant product 9. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 15B, 17F, 18C, 19A, 19F, 20, 22F, 23F, 33F, and from none to one or both of 6A and 25; the improvement wherein effectively immunogenic Type 22F pneumococcal polysaccharide is purified from a clarified fermentation lysate by the process of (a) fractionally precipitating with 0.25 to 0.75 volumes of alcohol, the lysate being at a pH of about 6.7 and having a final sodium acetate concentration of about 4% and being at a temperature of 2°-6° C., and removing contaminants so pricipitated, and (b) precipitating Type 22F polysaccharide with from about 1.25 to about 1.7 volumes of alcohol at a pH of about 6.7, and (c) collecting and redissolving such precipitate, and (d) repeating Step (a) at about 0.25 to 0.75 volumes of alcohol, and (e) repeating Step (b) at about 1.25 to 1.75 volumes of alcohol and repeating Step (c), and (f) fractionally precipitating the redissolved precipitate of (e) with hexadecyltrimethylammonium bromide at a temperature of from 21°-25° C. and a pH of 7.4±0.1, and a hexadecyltrimethylammonium bromide concentration of 2.0 to 5.0 volumes percent based on a 10% hexadecyltrimethylammonium brocide solution, (g) removing the precipitated polysaccharide and redissolving the polysaccharide in about 0.25M sodium chloride while chilled, and (h) reprecipitating the polysaccharide at a pH of about 6.7 with about 4% sodium acetate and about 1.5 volumes of alcohol, and redissolving in pyrogen-free water, and (i) repeating Step (h) 2 times, and (j) purifying the polysaccharide solution of (i) with activated charcoal at a pH of 6.1 and a sodium chloride concentration of 0.15M by adding activated charcoal in suspension to a concentration of from 3% to 7% based on a 20% activated charcoal suspension and the solution standing chilled for about 30 minutes and filtering out said activated charcoal, and (k) diafiltering the solution against distilled water, and (l) freezing and lyophilizing the resultant product.

10. In a multivalent pneumococcal vaccine comprising effective amounts of immunologically active purified pneumococcal capsular polysaccharide (substantially absent "C" polysaccharide) of pneumococcal types (Danish designation) consisting of 1, 2, 3, 4, 5, 6B, 7F, 8, 9N, 9V, 10A, 11A, 12F, 14, 17F, 18C, 19A, 19F, 20, 22F, 23F, 33F, and from none to one or both of 6A and 25; the improvement wherein effectively immunogenic Type 33F pneumonococcal polysaccharide is purified from a clarified fermentation lysate by the process of (a) fractionally precipitating with 0.25 to 0.75 volumes of alcohol, the lysate being at a pH of about 6.7 and having a final sodium acetate concentration of about 4% and being at a temperature of 2°-6° C., and removing contaminants so precipitated, and (b) precipitating Type 33F polysaccharide with from about 1.25 to about 1.75 volumes of alcohol at a pH of about 6.7, and (c) collecting and redissolving such precipitate, and (d) repeating Step (a) at about 0.25 to 0.75 volumes of alcohol, and
(e) repeating Step (b) and repeating Step (c) and
(f) fractionally precipitating impurities from the polysaccharide of (e) with hexadecyltrimethylammonium bromide at a temperature of from 21°–25° C. and 0.15M sodium chloride and a pH of 7.4+0.1, and a hexadecyltrimethylammonium bromide concentration of 1.0 to 5.0 volumes percent, based on a 10% hexadecyltrimethylammonium bromide solution, and
(g) reprecipitating the polysaccharide at a pH of about 6.7 with about 4% sodium acetate and about 1.5 volumes of alcohol, and redissolving in pyrogen-free water, and
(h) repeating step (g) 2 times, and
(i) purifying the polysaccharide solution of (h) with activated charcoal at a pH of 6.1 and a sodium chloride concentration of 0.15M, by adding activated charcoal in suspension to a concentration of from 3% to 7% based on a 20% activated charcoal suspension, and the solution standing chilled for about 30 minutes and filtering out said activated charcoal, and
(j) diafiltering the solution against distilled water, and
(k) freezing and lyophilizing the resultant product.

* * * * *